(12) United States Patent
Brown et al.

(10) Patent No.: US 8,859,295 B2
(45) Date of Patent: Oct. 14, 2014

(54) SYSTEM AND METHOD TO MEASURE DISSOCIATION CONSTANTS

(75) Inventors: Richard Brown, East Falmouth, MA (US); Burleigh Hutchins, West Brookfield, MA (US); Ernesto Freire, Baltimore, MD (US)

(73) Assignee: AVIA Biosystems, LLC, East Falmouth, MA (US)

( * ) Notice: Subject to any disclaimer, the term of this patent is extended or adjusted under 35 U.S.C. 154(b) by 614 days.

(21) Appl. No.: 13/214,355

(22) Filed: Aug. 22, 2011

(65) Prior Publication Data

US 2012/0045849 A1 Feb. 23, 2012

Related U.S. Application Data

(60) Provisional application No. 61/375,920, filed on Aug. 23, 2010.

(51) Int. Cl.
*G01N 33/566* (2006.01)
*G01N 35/10* (2006.01)
*G01N 33/68* (2006.01)

(52) U.S. Cl.
CPC ........ *G01N 33/6803* (2013.01); *G01N 35/1065* (2013.01); *G01N 35/1072* (2013.01)
USPC ............ 436/501; 435/7.1; 435/7.92; 436/517

(58) Field of Classification Search
None
See application file for complete search history.

(56) References Cited

U.S. PATENT DOCUMENTS

| | | | |
|---|---|---|---|
| 6,232,085 B1 | 5/2001 | Pantoliano et al. | |
| 2004/0157266 A1 | 8/2004 | Oas et al. | |
| 2007/0099305 A1* | 5/2007 | Oas et al. | 436/514 |
| 2009/0298186 A1 | 12/2009 | Brigham-Burke et al. | |
| 2011/0124120 A1* | 5/2011 | Kranz et al. | 436/501 |

OTHER PUBLICATIONS

Nuss et al., Denaturation of replication protein A reveals an alternative conformation with intact domain structure and oligonucleotide binding activity, Protein Science 13, 2004, pp. 1365-1378.*
Journal of the Korean Chemical Society, 2005, vol. 49, No. 5, pp. 479-487, "Analysis of the m-value Change in the Equilibrium Unfolding of Hydrophobic Core Variant Ubiquitin", Park, et al.
International Search Report/Written Opinion mailed Apr. 9, 2012 in co-pending PCT application No. PCT/US2011/048799.

* cited by examiner

*Primary Examiner* — Gary W Counts
(74) *Attorney, Agent, or Firm* — Nields, Lemack & Frame, LLC

(57) ABSTRACT

A system and method for determining the dissociation constant for a particular ligand is disclosed. In accordance with certain embodiments, the method creates a chemical denaturation curve of a protein in the absence of the ligand. A particular point is selected from this curve, such as the point at which 90% of the protein is unfolded. The molarity of chemical denaturant is determined for this selected point. A one point test is then performed for the protein with a predetermined concentration of the particular ligand. The fraction of protein which is unfolded at this point is then used to determine the dissociation constant for the ligand. This constant is used to quickly determine whether a particular ligand is well suited to be considered a potential drug candidate against that protein target.

6 Claims, 5 Drawing Sheets

SYSTEM AND METHOD TO MEASURE DISSOCIATION CONSTANTS

This application claims priority from U.S. Provisional Patent Application Ser. No. 61/375,920, filed Aug. 23, 2010, the disclosure of which are incorporated herein by reference in its entirety.

BACKGROUND OF THE INVENTION

The first step in the development of new drugs is the identification of molecules that bind to the target protein with relatively high affinity. This first step is usually accomplished by screening large libraries of compounds or fragments that can be used as starting points for optimization into potential drug candidates. In the case of enzyme targets, inhibition assays are usually implemented in a high throughput format in order to identify those compounds that exhibit the highest inhibition at a given concentration. In the case of non-enzyme targets, the situation is compounded by the absence of an intrinsic activity and compound binding becomes the most reliable observable for screening. In all cases (enzymes and non-enzymes) however, inhibitors need to bind to the target. Therefore, identifying those compounds that bind to the target with the highest affinity is a critical step in the identification of drug candidates. High throughput direct binding assays to arbitrary proteins have been difficult to implement. An alternative is to measure the effects of binding on specific protein properties. One such property is the structural stability of the native state of the protein. Ligands that bind to the native state of the protein will stabilize that structure; consequently, by measuring the stabilization effect of a compound on the protein target, it is possible to identify compounds that bind to the target protein. Furthermore, by measuring the magnitude of the stabilization effect, it is possible to rank the binding affinity of a library of compounds.

There are different ways to measure protein stability and each involves disrupting the protein structure through either physical or chemical means. This disruption of the protein structure is referred to as denaturation.

Temperature is one of the most widely used physical denaturants. In this scenario, a protein is subjected to increasing temperature and the corresponding changes in its structure are recorded. One of the disadvantages of temperature denaturation is that proteins typically denature at temperatures at or above 60° C. However, in most instances, the temperatures of interest are physiological (about 37° C.), room (about 25° C.) and storage (4° C.). Thus, results from temperature-based denaturation tests must be extrapolated by more than 25° C. to understand the effects at the temperatures of interest. Compounds identified by monitoring the temperature stabilization of a protein reflect the binding affinity at the denaturation temperature rather than the binding affinity at the physiological temperature. The rank order is, most of the time, different due to different temperature dependences of the binding affinity as expected from differences in the binding enthalpy.

A second way to measure protein stability is through the use of chemical denaturants, such as urea or guanidine hydrochloride. This method permits measurements to be done at any desired temperature.

The structural stability of a protein is determined by its Gibbs energy of stability, $\Delta G$. This value, $\Delta G$, is a function of temperature, chemical denaturants and other physical and chemical variables. Using the common example of a two state model, where a protein is either folded (i.e. native) or unfolded (i.e. denatured), the protein can transition between these two states:

$N \Leftrightarrow U$, wherein N is the native (folded) state and U is the unfolded state.

Two different rate constants can be defined from this transitional equation. $K_f$ is the rate of the folding reaction; while $K_u$ is the rate of the unfolding reaction. Finally, the equilibrium constant, K, can be defined as the ratio of the unfolding rate to the folding rate, or $$K = \frac{K_u}{K_f}.$$

Furthermore, the Gibbs energy can be expressed in terms of K, as $$\Delta G = -RT \ln(K),$$

where R is the gas constant, T is the temperature, expressed in Kelvin and ln(K) is the natural log of K. Thus, if K is greater than one, the protein unfolds at a higher rate than it folds, and its Gibbs energy is negative. Conversely, if K is less than one, the protein unfolds at a slower rate than it folds, and its Gibbs energy is positive. Also, K is equal to the ratio of the concentration of protein in the unfolded state and the concentration of protein in the folded state K=[U]/[F].

In addition, it has been observed that, for chemical denaturants, a nearly linear relationship exists between the Gibbs energy and the concentration of the denaturant. This relationship may be expressed as $$\Delta G = \Delta G_0 - m^*[\text{denaturant}],$$

where $\Delta G_0$ is the intrinsic Gibbs energy, [denaturant] is the concentration of denaturant, and m is the multiplier, which is unique for a particular protein.

In the presence of a ligand, the Gibbs energy becomes:

$$\Delta G = \Delta G_0 - m^*[\text{denaturant}] + RT \ln(1+[L]/K_d)$$

where $K_d$ is the binding dissociation constant of the ligand and [L] the free concentration of the ligand.

For a native/unfolded equilibrium, the fraction of protein molecules which are unfolded, or denatured, $F_d$, is given by:

$$F_d = \frac{K}{1+K},$$

where K is the equilibrium constant.

This equation can be used to allow calculation of a denaturation curve. When a protein changes from its folded state to an unfolded state, certain measurable characteristics of the protein also change. One such characteristic is the fluorescence of the protein.

FIG. 1 shows a typical urea denaturation curve for an antibody. The y, or vertical, axis is a measure of the intrinsic fluorescence of the protein. The fluorescence of different dyes, usually known as protein probes, can also be used. The horizontal, or x, axis is the concentration of urea in solution with the protein. As can be seen, at a certain point, between 3M and 4M urea, the fluorescence of the protein changes dramatically, indicating that it has denatured.

While the preferred embodiment described in this application utilizes fluorescence emission (intrinsic or extrinsic) as a way to determine the degree of denaturation or unfolding of a protein, the disclosure is not limited to this technique. There are many physical observable properties and their associated instrumentation, in addition to fluorescence spectroscopy, that are sensitive to the degree of denaturation of a protein.

These observable properties include, but are not limited to uv/vis spectroscopy, circular dichroism, nuclear magnetic resonance (NMR), infrared spectroscopy (IR) among others.

The generation of the data needed to produce such a graph is laborious. In one scenario, a solution containing the protein and any excipients is prepared. A sample of this solution is then subjected to fluorescent light and the emission is recorded. This is the baseline fluorescence with no chemical denaturant. In some embodiments, an amount of urea is then added to the remainder of the solution, and the light test is repeated on a portion of this modified solution. An additional amount of urea is then added to the remainder of the solution and a third light test is performed. This process is repeated for the number of desired samples. The amount of urea added each time is a function of the desired granularity of the test, and the range of urea molarities to be included. Such a method is prone to errors, as there are cumulative errors due to the constant addition of urea to the remaining solution. In this stepwise urea addition method, the process will result in the dilution of the protein and also a smaller fluorescence signal. In addition, since the solubility of urea is about 10.5M and a final 8M urea concentration is needed, the starting protein solution volume needs to be extremely small. The protein will be significantly diluted as the experiment progresses.

In another embodiment, a plurality of solutions, each with the protein, any excipients, and the proper amount of urea, is individually prepared. Each of these prepared solutions is then light tested to determine its fluorescence. While this method removes the cumulative errors associated with the previous method, it is extremely time consuming, especially for a large number of samples.

The resulting graph, such as that shown in FIG. 1, shows the stability of a particular combination of buffer, ligand and excipient conditions in the presence of a chemical denaturant. More stable combinations have a similarly shaped graph, shifted to the right. Conversely, less stable combinations have a graph shifted to the left. The presence of ligands that bind to the native state of the protein shifts the graph to the right. The magnitude of the shift is proportional to the concentration of ligand and the binding affinity of the ligand. By determining the magnitude of the shift for different potential ligands that are screened at the same concentration, it is possible to rank them in terms of their binding affinities. This is a most important goal in drug development as it provides the basis for the identification of potential drug candidates. Traditionally, full denaturation curves have been used which can be time consuming when thousands of potential ligands are screened.

It would be beneficial to create a method of identifying potential ligands which is less laborious than current processes.

SUMMARY OF THE INVENTION

A system and method for determining the dissociation constant for a particular ligand is disclosed. In accordance with certain embodiments, the method creates a chemical denaturation curve of a protein in the absence of the ligand. A particular point is selected from this curve, such as the point at which 90% of the protein is denatured, or unfolded. The molarity of chemical denaturant is determined for this selected point. A one point test is then performed for the protein with a predetermined concentration of the particular ligand. The fraction of protein which is unfolded at this point is then used to determine the dissociation constant for the ligand. This constant is determined for any potential ligands in order to identify those that bind with the highest affinity.

DETAILED DESCRIPTION OF THE INVENTION

Often of interest is the binding affinity of a ligand to a protein. This affinity is often referred to as the dissociation constant ($K_d$). For a ligand-protein equilibrium, the equilibrium equation may be expressed as:

$$L + P \Leftrightarrow LP,$$

where L is the ligand, P is the protein and LP is used to represent a complex where the ligand and protein are binded together.

The dissociation constant is defined as:

$$K_d = \frac{[L][P]}{[LP]},$$

where [L] is the concentration of ligand, [P] is the concentration of protein, and [LP] is the concentration of the complex where the ligand and protein are binded together.

The dissociation constant is a measure of how tightly the protein and ligand bind to one another. Lower values of $K_d$ indicate a high affinity, while high values of $K_d$ indicate weak affinity. In pharmaceutical applications, it is often beneficial to know the dissociation constant for a particular set of proteins and ligands. The present method provides a relatively quick and simple method of estimating this value.

Figure 1:
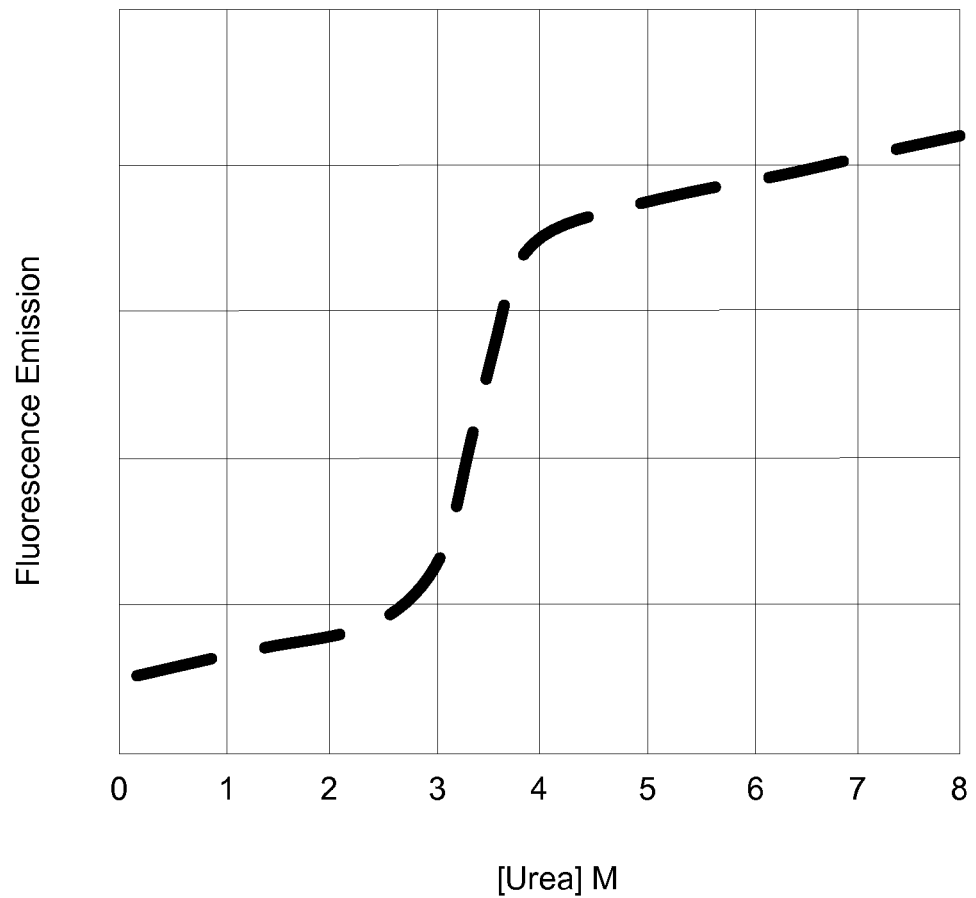
FIG. 1 is a denaturation graph of the prior art.

FIG. 1 shows a typical denaturation graph, used to determine the stability of a protein in the presence of a chemical denaturant. This graph shows the stability of the protein for a particular combination of buffer, ligand and excipients conditions. However, such a denaturation graph may consist of a large number of points, such as 24 or more, which requires testing time. It is useful to estimate the binding affinity of a particular ligand without the need to create a complete denaturation graph. This is especially true in a screening scenario where a large number of compounds need to be evaluated.

In one embodiment, a buffer solution is prepared, which comprises the protein of interest and any excipients. In this embodiment, no ligand is added to the buffer solution.

A denaturation curve is created, where a chemical denaturant, such as urea, is used to cause the protein to unfold. To do this, one may create two different formulations:

Formulation 1: solution with protein and excipients and no ligand and no denaturant Formulation 2: solution with protein and excipients and no ligand and maximum denaturant While the descriptions in this disclosure refer to certain formulations having no denaturant, it is understood that, in another embodiment, Formulation 1 contains a minimum amount of denaturant, which may be greater than 0, while Formulation 2 contains a maximum amount of denaturant.

Figure 2:
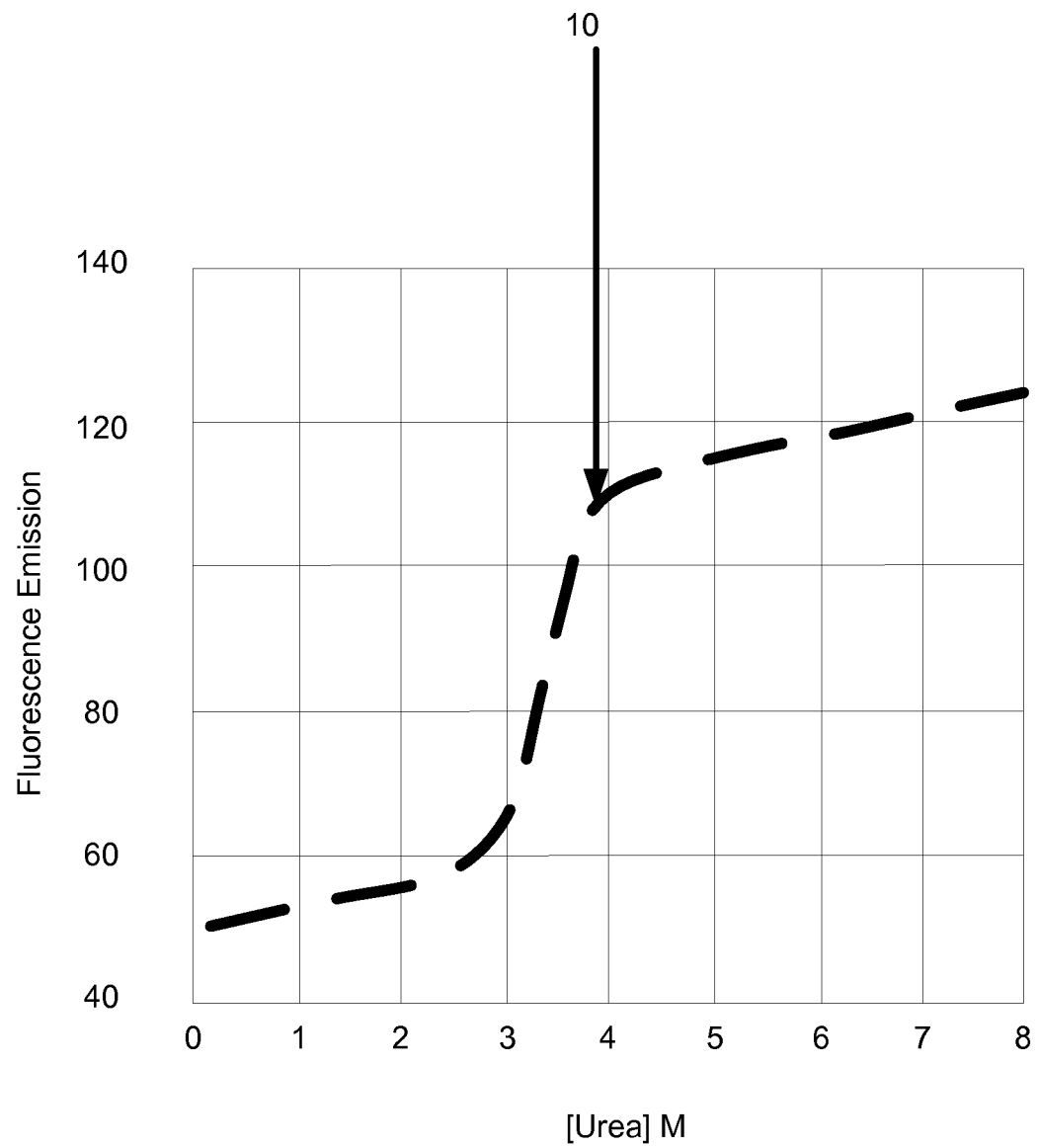
FIG. 2 is a graph of a denaturation graph, showing a point of interest where the fraction of the protein that is denatured is equal to a predetermined amount.

To create a denaturation graph, one may begin by using formulations 1 and 2. By combining these two formulations in different proportions, one can create a plurality of solutions, each having identical protein and excipients and a varying amount of chemical denaturant. This plurality of solutions can be used to create a first denaturant graph, shown as shown in FIG. 2.

Using this created denaturation graph, a point of interest is selected. This point represents the molarity at which the fraction of the protein that has denatured (or unfolded) is equal to a predetermined amount ($F_d$). The terms "denatured" and "unfolded" are used interchangeably in this disclosure. In some embodiments, the point at which 90% of the protein has unfolded is used, while in other embodiments, the predetermined denatured fraction ($F_d$) is different, such as 80%, 70%, or a lower value. FIG. 2 shows a sample denaturation graph, with the sample point 10 selected at a predetermined denatured percentage ($F_d$) of 90%.

The molarity of chemical denaturant at the point of interest is recorded. In this example, this determined molarity is about 4M. In other examples, this point may correspond to a different molarity, which may be greater or less.

Figure 3:
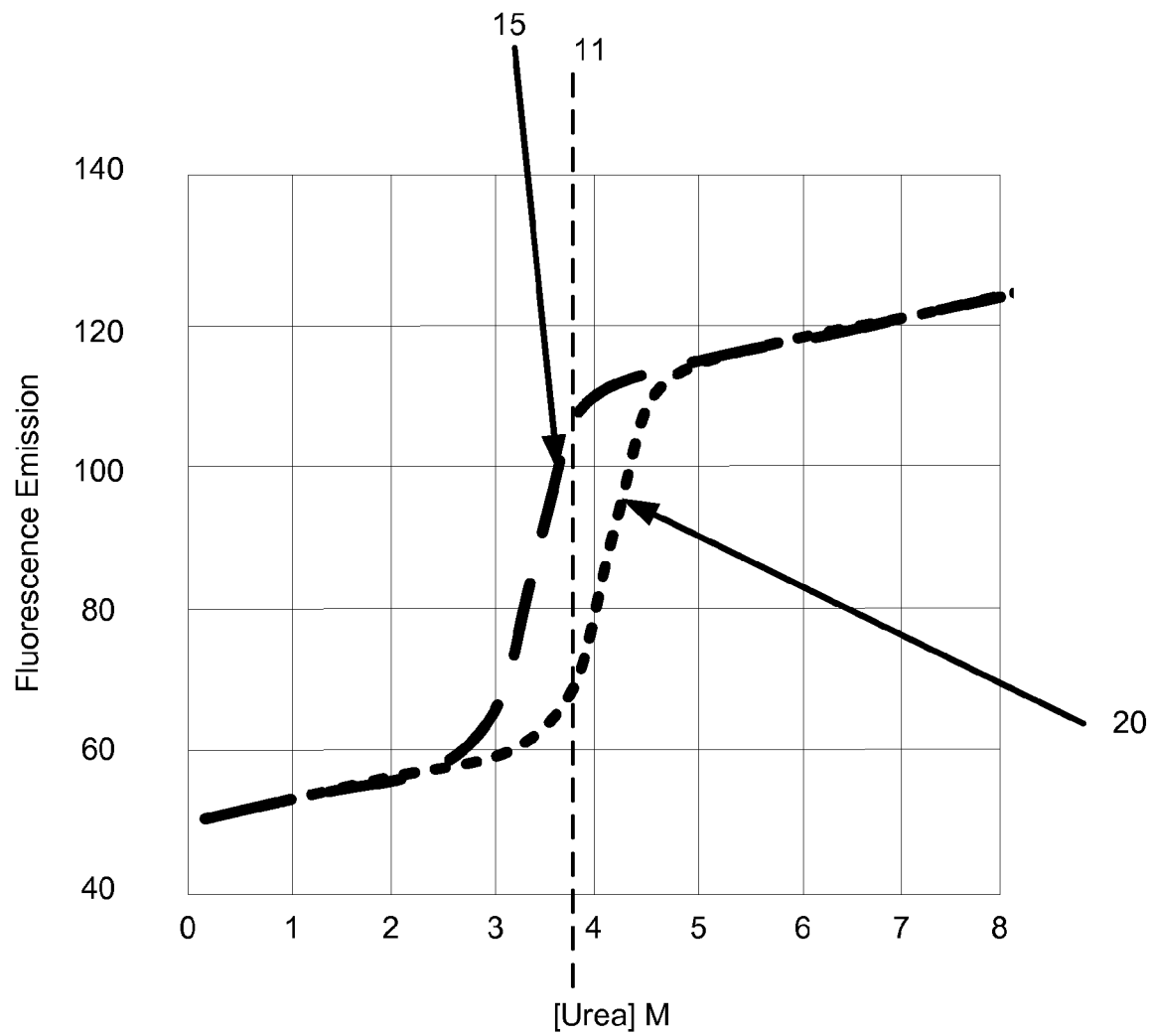
FIG. 3 is a graph showing the denaturation graph of FIG. 2 and a denaturation graph with a ligand added to the buffer solution.

Various experiments may then be performed at this previously determined denaturant concentration. In each experiment, a particular ligand at a specific concentration is combined with the buffer with the previously determined denaturant concentration. In the presence of a ligand, the protein will be more stable, therefore shifting the denaturation curve to the right. Although an entire denaturation graph is not created for the ligand, FIG. 3 shows an example of such a denaturation curve 20 superimposed on the original denaturation graph 15. Dotted line 11 shows the previously determined molarity of denaturant that caused 90% of the protein to become denatured (unfolded) on original denaturation graph 15. The ligand provides stability, which causes the fraction of denatured protein at this previously determined molarity to be reduced for line 20.

However, as stated above, a complete denaturation curve 20 is not required. Rather, the selected ligand at a specified concentration is put into a buffer solution having the previously determined concentration of chemical denaturant. The fraction of protein that is denatured in the presence of the ligand ($F_{d,l}$) is then recorded.

This recorded fraction of denatured protein is then used to determine the dissociation constant ($K_d$). The dissociation constant is determined based on the concentration of the ligand, the predetermined denatured fraction ($F_d$), and the fraction of protein that is unfolded in the presence of the ligand ($F_{d,l}$). This relationship may be expressed as:

$$K_d = \frac{[L]}{A * \frac{1 - F_{d,l}}{F_{d,l}} - 1},$$

where [L] is the concentration of the ligand and A is defined as $$\frac{F_d}{1 - F_d}.$$

Figure 4:
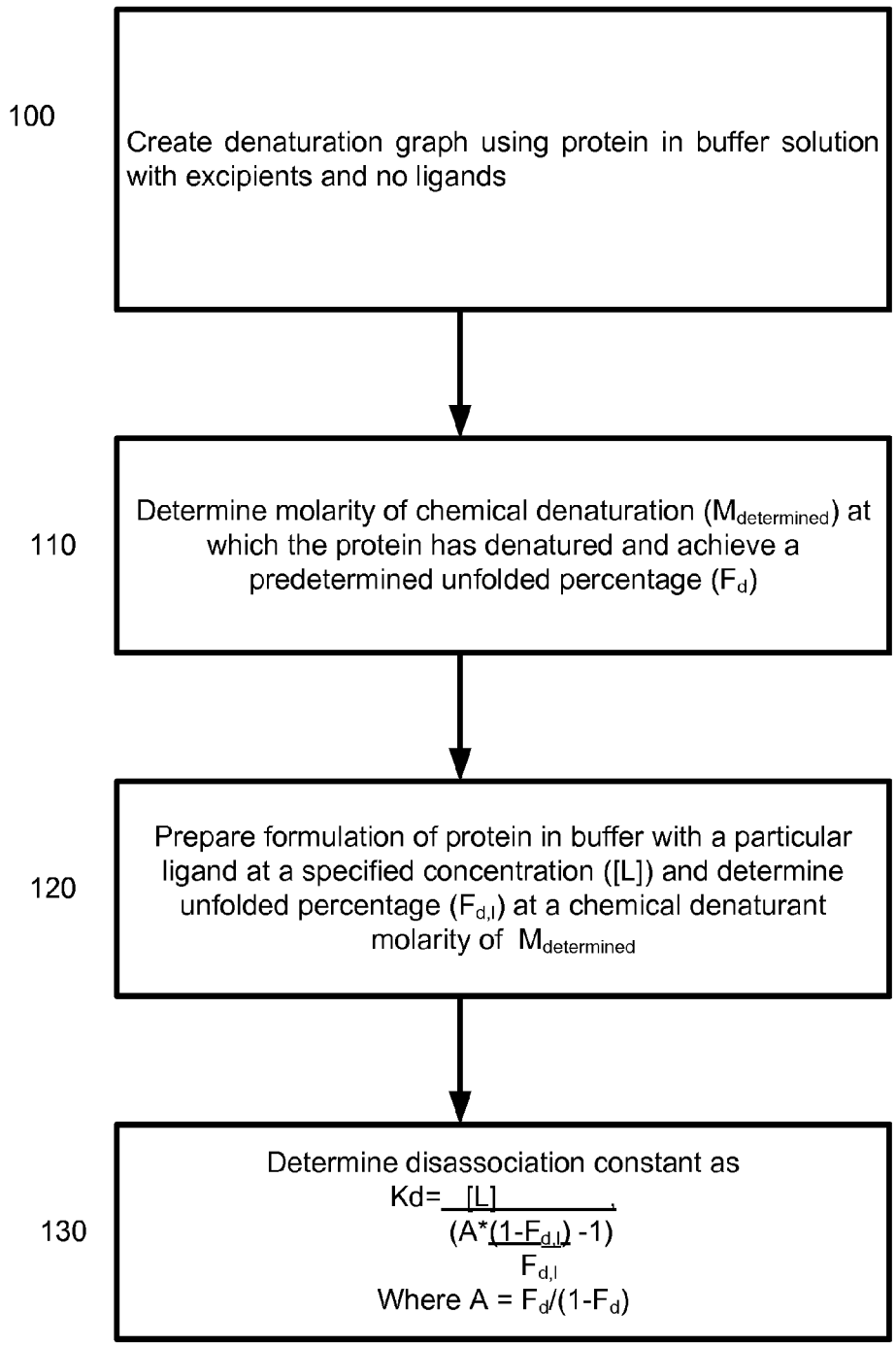
FIG. 4 is a flowchart illustrating a process to determine the dissociation constant for a ligand.

FIG. 4 shows a flowchart showing the steps of the present method. First, in step 100, a denaturation graph is generated for a protein in buffer solution with no ligand. The molarity of chemical denaturation needed to achieve a predetermined folding percentage ($F_d$) is then determined, based on the graph generated in step 100. This molarity of chemical denaturant ($M_{determined}$) is then used to test one of more concentrations and ligands to determine the various dissociation constants.

As shown in step 120, a formulation of the protein with the particular ligand at a specified concentration ([L]) is created. The unfolded (or denatured) percentage of the protein with ligand (Fd,l) is then determined at the previously selected chemical denaturant molarity.

These various terms, (Fd,l, Fd, [L]) are then used to determine the dissociation constant of the ligand/protein complex. As noted above, lower values indicate higher levels of affinity between the ligand and the protein.

Those ligands and concentrations which show promise, as determined based on the one point test described above, can then be further evaluated. In one embodiment, a full denaturation graph, such as that shown in FIG. 2, is created from the particular protein and ligand complex. Similarly, those ligands which were determined to have higher dissociation constants than a predetermined threshold, may be discarded and not included in further study or evaluation.

Therefore, the above method provides a rapid and accurate technique to quickly determine the dissociation constant for a ligand/protein complex. This dissociation constant can then be used as a basis to decide whether a particular ligand should be further studied or evaluated, or whether that ligand should be disregarded.

This technique may be performed manually, in that the creation of the denaturation curve and selection of the fraction denatured ($F_d$) may be performed manually with the aid of a detector to measure the observable property. In addition, the creation of the various ligands having the determined amount of denaturant may also be done manually. In another embodiment, the technique described herein may be performed in an automated manner, in that the creation of the denaturation curve and the preparation and testing of the various samples can be performed using an automated process.

Figure 5:
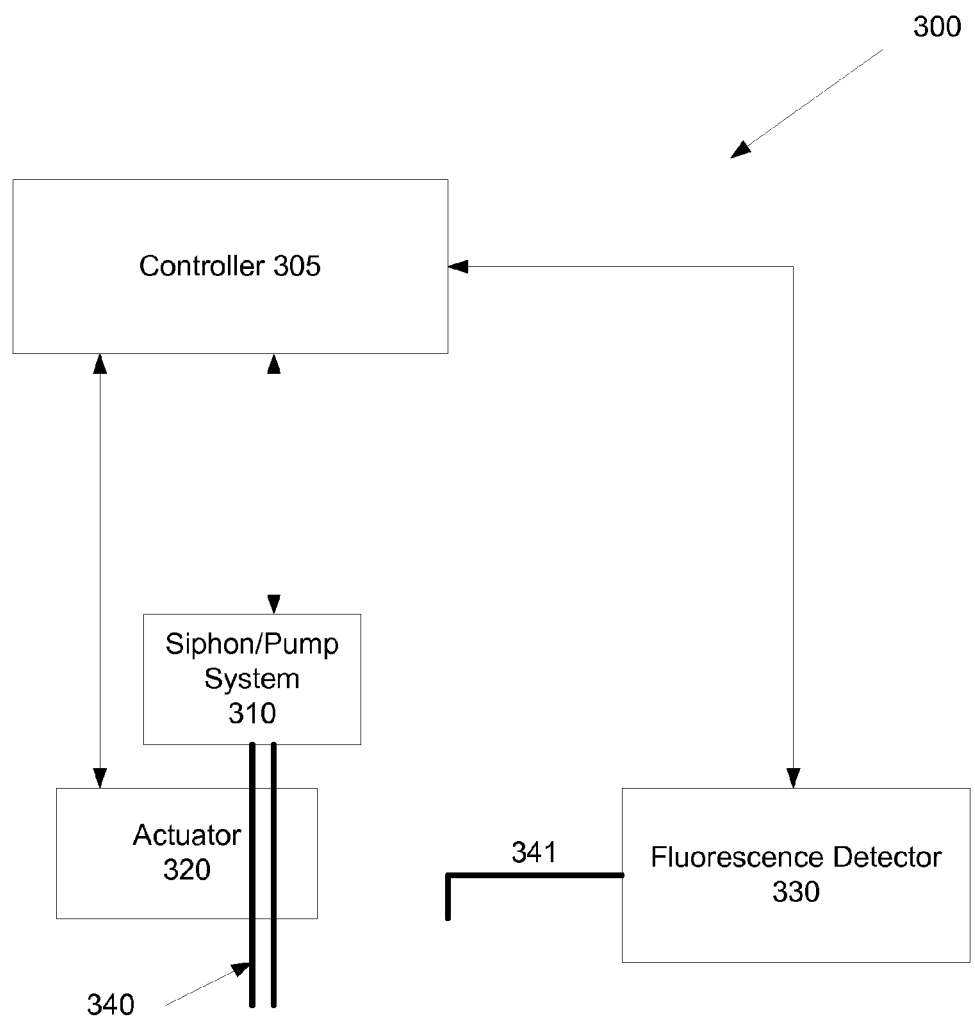
FIG. 5 is a block diagram of an apparatus adapted to perform the methods of FIG. 4.

In this embodiment, shown in FIG. 5, an apparatus 300 having a controller 305 with a processing unit and a storage element is used. The storage element may be RAM, DRAM, ROM, Flash ROM, EEROM, magnetic media, or any other medium suitable to hold computer readable data and instructions. The instructions may be those necessary to execute the flowchart of FIG. 4. The processing unit may be a dedicated microcontroller, a personal computer or any other suitable computing device. In addition, the apparatus has a pump or siphon system 310, which allows it to extract liquid from a variety of wells in exact quantities and mix these liquids together, preferably in another well. The apparatus 300 also has a means to measure and record the fluorescence of the formulations, such as by using a cannula 341 to draw liquid into a commercially available fluorescence detector 330. The apparatus also includes one or more actuators 320 which can move cannulas 340 from one position to another, so as to draw fluid from a first well and expel the fluid into a second well. These cannulas 340 can be used to prepare the formulations needed to create a denaturation graph, and to prepare the formulation of protein in buffer, shown in step 120 in FIG. 4.

The present disclosure is not to be limited in scope by the specific embodiments described herein. Indeed, other various embodiments of and modifications to the present disclosure, in addition to those described herein, will be apparent to those of ordinary skill in the art from the foregoing description and accompanying drawings. Thus, such other embodiments and modifications are intended to fall within the scope of the present disclosure. Further, although the present disclosure has been described herein in the context of a particular implementation in a particular environment for a particular purpose, those of ordinary skill in the art will recognize that its usefulness is not limited thereto and that the present disclosure may be beneficially implemented in any number of environments for any number of purposes.

What is claimed is:

1. A method of determining the dissociation constant ($K_d$) for a particular protein and ligand combination, comprising:
   providing a first solution comprising said protein with no ligand and a predetermined minimum amount of chemical denaturant; and a second solution comprising said protein, no ligand and a predetermined maximum amount of said chemical denaturant;
   mixing said first and second solution in a plurality of samples, each having said first and second solution in different proportions to create solutions having different molarities of said chemical denaturant;
   measuring an observable property of each of said plurality of samples;
   creating a denaturation graph based on said observable property and said molarity;
   determining the molarity at which a predetermined fraction of said protein molecules became denatured ($F_d$);
   preparing a third solution comprising said protein and a ligand at a specified concentration ([L]) and an amount of chemical denaturant equal to said determined molarity;
   measuring said observable property of said third solution to determine a fraction of said protein molecules that became denatured in the presence of said ligand ($F_{d,l}$); and
   using said specified concentration ([L]), said predetermined fraction ($F_d$) and said fraction of said protein molecules that became denatured in the presence of said ligand ($F_{d,l}$) to determine said dissociation constant for said particular protein and ligand combination, wherein said dissociation constant ($K_d$) is calculated from the formula:

$$K_d = \frac{[L]}{A * \frac{1 - F_{d,1}}{F_{d,1}} - 1},$$

where A is defined as $$\frac{F_d}{1 - F_d}.$$

2. The method of claim 1, wherein said observable property is fluorescence.

3. The method of claim 1, wherein said predetermined minimum amount of chemical denaturant comprises no denaturant.

4. The method of claim 1, further comprising subjecting said ligand to further study, based on said dissociation constant.

5. The method of claim 1, further comprising discarding said ligand, based on said dissociation constant.

6. The method of claim 4, wherein said further study comprises performing a full denaturation graph with said ligand at said specified concentration,
   wherein said full denaturation graph is generated by:
   providing a first solution comprising said protein with said specified concentration of ligand and a predetermined minimum amount of chemical denaturant; and a second solution comprising said protein, said specified concentration of ligand and a predetermined maximum amount of said chemical denaturant;
   mixing said first and second solution in a plurality of samples, each having said first and second solution in different proportions to create solutions having said specified concentration of ligand and different molarities of said chemical denaturant;
   measuring an observable property of each of said plurality of samples; and
   creating said full denaturation graph based on said observable property, said specified concentration and said molarity.

* * * * *